US010245063B2

(12) United States Patent
Loreth

(10) Patent No.: US 10,245,063 B2
(45) Date of Patent: Apr. 2, 2019

(54) SURGICAL DRIVE APPARATUS

(71) Applicant: Smith & Nephew, Inc., Memphis, TN (US)

(72) Inventor: Brian Loreth, Braintree, MA (US)

(73) Assignee: Smith & Nephew, Inc., Memphis, TN (US)

( * ) Notice: Subject to any disclaimer, the term of this patent is extended or adjusted under 35 U.S.C. 154(b) by 282 days.

(21) Appl. No.: 15/113,262

(22) PCT Filed: Jan. 26, 2015

(86) PCT No.: PCT/US2015/012826
§ 371 (c)(1),
(2) Date: Jul. 21, 2016

(87) PCT Pub. No.: WO2015/112938
PCT Pub. Date: Jul. 30, 2015

(65) Prior Publication Data
US 2017/0020545 A1    Jan. 26, 2017

Related U.S. Application Data

(60) Provisional application No. 61/931,867, filed on Jan. 27, 2014.

(51) Int. Cl.
*A61B 17/14*    (2006.01)
*A61B 17/32*    (2006.01)
*A61B 17/00*    (2006.01)

(52) U.S. Cl.
CPC .............. *A61B 17/32002* (2013.01); *A61B 2017/00477* (2013.01); *A61B 2017/00539* (2013.01);

(Continued)

(58) Field of Classification Search
CPC ... A61B 17/24; A61B 17/32; A61B 17/32002; A61B 17/162; A61B 17/00234;
(Continued)

(56) References Cited

U.S. PATENT DOCUMENTS 6,293,957 B1    9/2001   Peters et al.
2004/0220602 A1*  11/2004  Deng ............... A61B 17/32002
                                                        606/170

FOREIGN PATENT DOCUMENTS

DE    102010050352    5/2012
EP        0286415    10/1988
WO     2012135087    10/2012

OTHER PUBLICATIONS

International Search Report for PCT/US2015/012826, dated Aug. 4, 2015.

* cited by examiner

*Primary Examiner* — David C Eastwood
*Assistant Examiner* — Mohamed G Gabr

(57) ABSTRACT

A surgical drive apparatus includes a rotating shaft of a sectioning device and a drive unit having a motor disposed in a motor chamber, in which the motor rotationally couples to the rotating shaft as the rotating shaft extends through an end of the motor chamber. A suction chamber is defined by an interior of a cap, in which the end of the motor chamber is receptive to the cap for sealing engagement with the drive unit, and a rotary tool such as the sectioning device extends through the cap for rotational movement relative to the cap while maintaining fluid communication with the suction chamber. For evacuation of surgical material, an outflow tube is in fluid communication with the suction chamber for providing a fluid path to the suctioning device via the suction chamber. The drive protrudes from the motor chamber which is sealed to allow cleaning and sterilization.

7 Claims, 8 Drawing Sheets

(52) U.S. Cl.
CPC ............ *A61B 2017/320032* (2013.01); *A61B 2217/005* (2013.01)

(58) Field of Classification Search
CPC ............ A61B 17/1624; A61B 17/1628; A61B 17/1633; A61B 17/320016; A61B 17/3498; A61B 2017/00477; A61B 2017/0046; A61B 2017/00367; A61B 2017/00539; A61B 2017/0023; A61B 2217/005; A61B 2217/007; A61B 10/025; A61B 10/0283; A61B 18/1485; A61B 2010/0208; A61B 17/320783; A61B 17/320791; A61B 17/320758; A61F 9/00763; A61M 1/0064; A61M 3/0258
See application file for complete search history.

SURGICAL DRIVE APPARATUS

BACKGROUND

Motor drive units (MDUs) are often employed with a variety of surgical tools via a connection interface for imparting a rotation to a blade or ablation tool for engagement with a surgical site, typically for resection or the manipulating and removal of tissue. Often the tool employs a cannulated shaft or other passage for providing suction to the surgical site for evacuation of surgical material. In conventional approaches, the connection interface is typically in contact with fluid from the surgical site via a suction path. Surgically contaminated instruments must either be disposed of or sterilized in an autoclave to counter the risk of infection. Moreover, the contact with the fluid and the exposure to autoclaving for sterilization presents a problem with possible leakage into the motor chamber, which should remain dry to promote longevity of the motor powering the drive unit.

SUMMARY

A surgical drive apparatus includes an external rotating shaft adapted for engagement with a sectioning device and a drive unit having a motor disposed in a motor chamber, in which the motor rotationally couples to the rotating shaft as the rotating shaft extends through an end of the motor chamber for engagement with a surgical instrument or tool on a front surface of the drive unit housing. The external drive mechanism features an integrated non-circular interface to connect to the insertable resection device, such as a blade, burr or other sectioning device, and may be an oval, hex or any other non-circular geometric shape so as to impart rotary motion. The drive feature may be a receptacle or protrusion (male/female) and engageable directly to the rotating portion of the resecting device. A suction chamber is defined by an interior of a cap, in which the front surface (end) of the motor chamber is receptive to the cap for sealing engagement with the drive unit, and a rotary tool such as a sectioning device extends through the cap for rotational movement relative to the cap while maintaining fluid communication with the suction chamber. The rotating shaft of the MDU therefore engages the sectioning device for rotation therewith. The engagement is accomplished directly with the inner rotating shaft without the need for an additional connector or interface such as a drive tang or sluff chamber. For evacuation of surgical material, an outflow tube is in fluid communication with the suction chamber for providing a fluid path to the suctioning or low pressure device via the suction chamber and attached via a fitting on the suction chamber.

In the proposed approach discussed herein, the drive externally protrudes from the front surface on a distal end of the MDU, which is sealed to allow cleaning and sterilization. A molded adapter that encompasses a connection interface for a disposable blade or burr features an integrated outflow fitting for providing suction control and cooling of the MDU motor. The disclosed configuration addresses the problem of providing an external drive mechanism that maintains cleanability and sterilizeability by avoiding recesses, fluid cavities and voids prone to accumulation of surgical material, yet accepts a rotating surgical device via a corresponding external integrated attachment feature capable of engaging the surgical devices.

Depicted below is an example system, method and apparatus for driving the rotary surgical instrument and imparting a low-pressure suction capability through the surgical instrument powered by the drive unit. The approach disposes a rotational seal between a drive unit housing and a receptacle driven by a motor in the drive unit housing, and attaches a cannulated surgical instrument to the receptacle. The receptacle has a non-circular shape such as an oval, square or hex for imparting a rotary motion to the instrument, and the receptacle has a fluidic path between the cannulation and a suction chamber. The fluidic path may be an orifice or hole aligning with an opening to the cannulated interior of the instrument, for example, and is such that it does not interfere with rotational engagement of the surgical instrument. A detachable cap is disposed in sealing engagement with the drive unit housing. The detachable cap and drive unit housing define the suction chamber, and the surgical instrument extends through a hole or bearing in the detachable cap. The cap is configured for applying a low pressure source to the suction chamber via a suction port, in which the suction chamber is in fluidic communication with the cannulated surgical instrument for evacuating surgical material to the low pressure source. The cap, receptacle, and a front face of the drive housing define the suction chamber through which the suction path extends from the surgical instrument to the suction chamber and out through the suction port.

BRIEF DESCRIPTION OF THE DRAWINGS

The foregoing and other features will be apparent from the following description of particular embodiments disclosed herein, as illustrated in the accompanying drawings in which like reference characters refer to the same parts throughout the different views. The drawings are not necessarily to scale, emphasis instead being placed upon illustrating the principles of the invention.

DETAILED DESCRIPTION

Configurations disclosed below include a motor drive unit (MDU) with an external drive mechanism that engages a disposable rotating surgical instrument such as a blade or burr. The device consists of a MDU housing with an integral motor chamber that is sealed off from the protruding drive shaft that directly connects to the disposable surgical instrument. An integral locking feature enables the rotatable resection devices to be connected.

The disposable surgical instrument consists of a polymeric cap with an outflow fitting encompassing an outer tube. The outer tube may be over-molded or heat staked into the cap. An inner blade or burr is inserted into the outer tube and the assembly can be attached to the MDU and locked by means of a pin and groove system. The assembly contains an outflow tube that is attached to the MDU housing and controlled via a flow control pinch valve. The integral locking feature enables the blade or burr to be connected without the added complexity of latches. The inner blade or burr connects directly with the external drive via a noncircular geometric feature without the need for an additional mating component such as a drive tang or sluff chamber.

The external drive MDU embodying the disclosed approach redirects the fluidic passage for evacuating the surgical material to a passage defined between the rotary appliance and the outflow fitting by the polymeric cap. Extracted surgical material is drawn from the appliance (typically through a cannulation or channel through the blade) into the polymeric cap passage or void and into the outflow fitting without entering the sealed drive unit or passing by the drive motor. An internal seal within the MDU segregates the rotating shaft from the motor, and an external seal engages the polymeric cap at a circumferential region of the end of the drive unit for providing a sealing engagement to maintain low pressure (i.e. suction).

The disclosed approach therefore maintains a fluidic channel or passage around the exterior of the MDU and eliminates internal cavities or voids in the suction path that may collect surgical material. This approach limits the fluidic path to single use instruments and exterior surfaces of the MDU, including the external drive feature, that are readily cleanable, such as by an autoclave or other sterilization method. The fluidic path is therefore limited to a rotary drive engagement on a frontend of the MDU within an area encapsulated by the exterior seal and the polymeric cap. MDU surface exposure to the fluid evacuation stream of surgical material is therefore limited to the front surface area defined by the exterior seal that compresses against the polymeric cap.

Figure 1A:
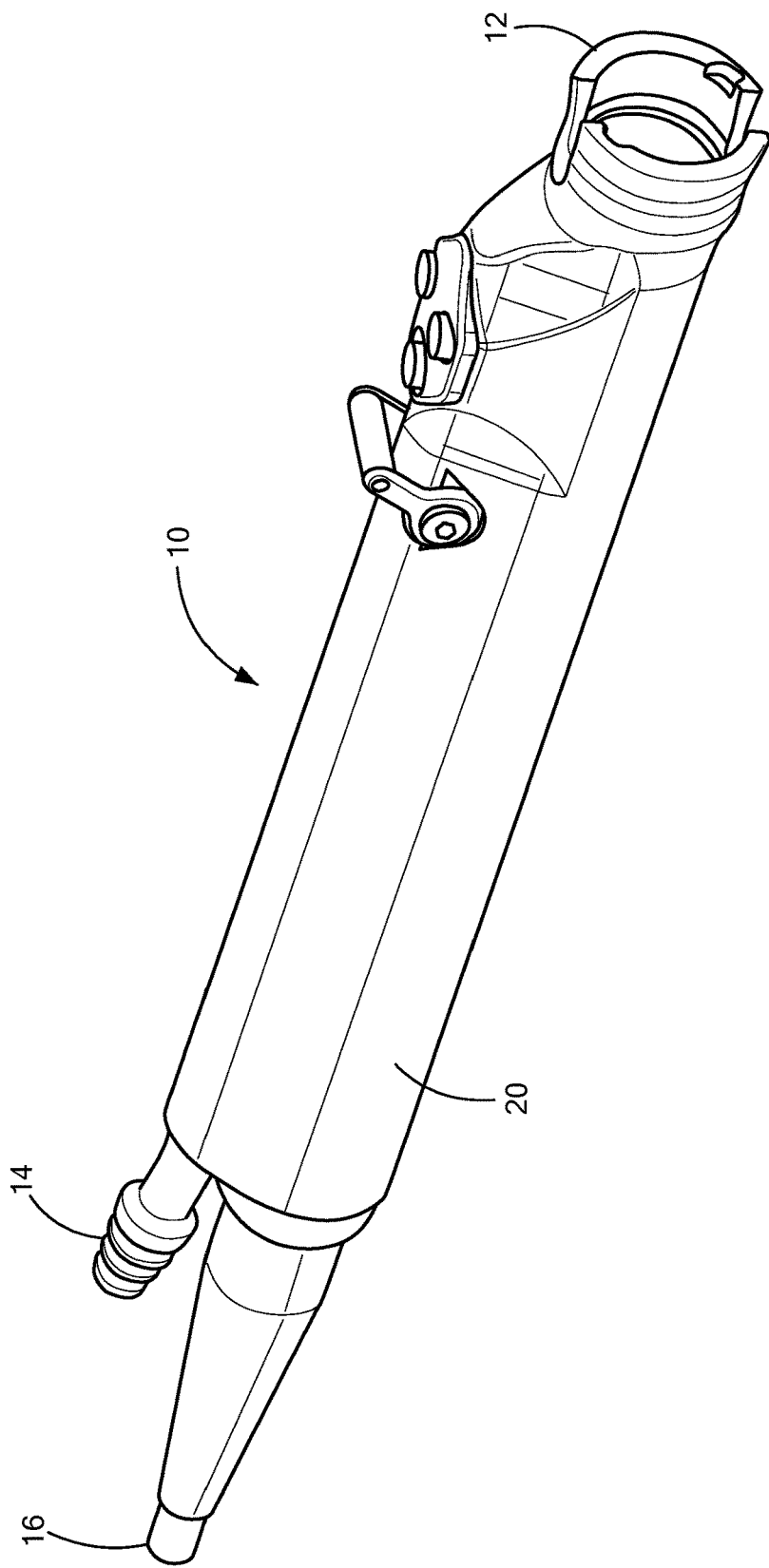
FIG. 1a is a conventional motor drive unit (MDU)

FIG. 1a is a conventional prior art motor drive unit (MDU). Referring to FIG. 1a, an MDU 10 typically includes a conventional appliance connector 12, for attaching surgical appliances for suction and rotary movement, a suction fitting 14, and a power supply cord or tube 16, for carrying electric, pneumatic or hydraulic power for driving the motor. The suction fitting 14 is in fluid communication with the appliance connector 12 through a motor housing 20, which comprises a substantial portion of the MDU 10. Various cavities and voids around the motor housing provide the fluid communication between the suction fitting 14 and appliance connector 12 for imparting suction to the surgical appliance so connected. Conventional approaches suffer from the shortcoming that these cavities and voids can tend to trap surgical fluid and material and may be difficult to clean, either via an autoclave or other process due to the enclosed nature of the conventional fluid path.

Figure 1B:
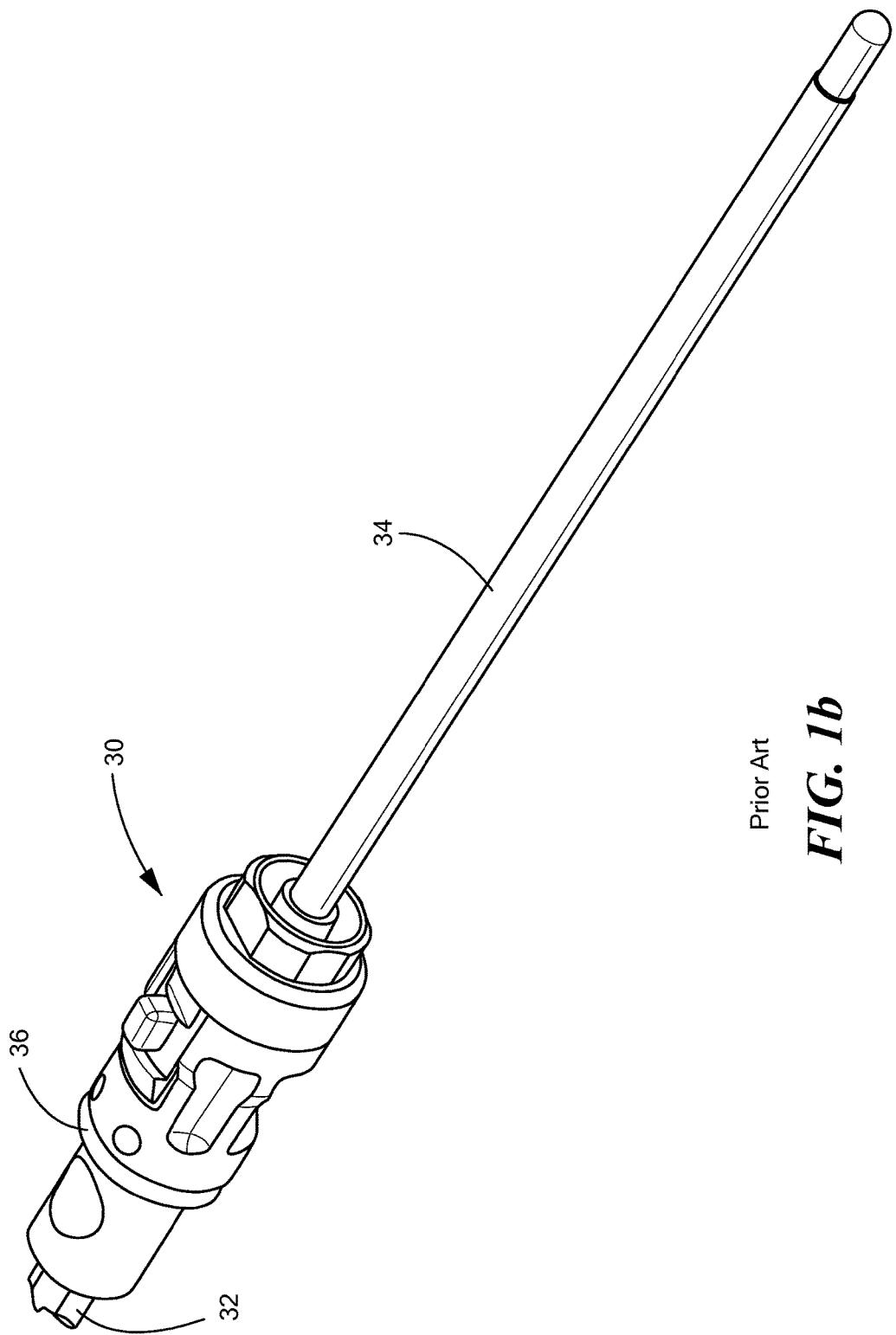
FIG. 1b is a conventional cutting tool engaged by the MDU of FIG. 1.

FIG. 1b is a conventional cutting tool engaged by the MDU of FIG. 1a. Referring to FIGS. 1 and 1b, a hub 30 includes a tang 32 that is adapted to engage the appliance connector 12 of the MDU 10. A conventional cutting shaft 34 attached to the hub 30 and rotates an inner blade concentrically within an outer blade for cutting tissue when driven by the tang 32. A seal 36 provides fluidic separation and sealing for suction via the MDU. The conventional cutting tool therefore requires a plurality of molded parts, including the tang 32 and an associated attachment to the hub 30, and the hub 30 employs components for fixing the hub 30 in rotational communication with the cutting shaft 34 for rotation when driven by the tang 32. Each of these additional components requires cleaning and sterilization for multi-use contexts, or single use disposable construction, which tends to increase per-use costs.

Figure 2:
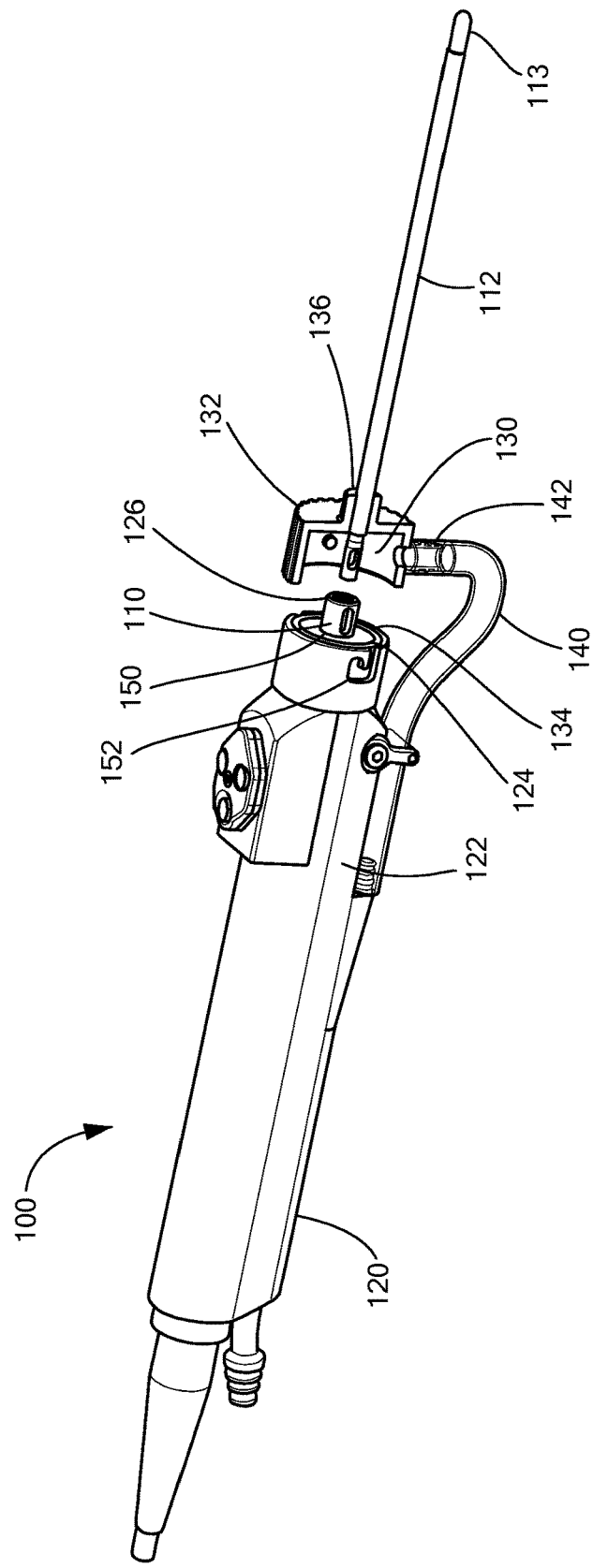
FIG. 2 is a perspective view of the external MDU as disclosed herein.
Figure 3A:
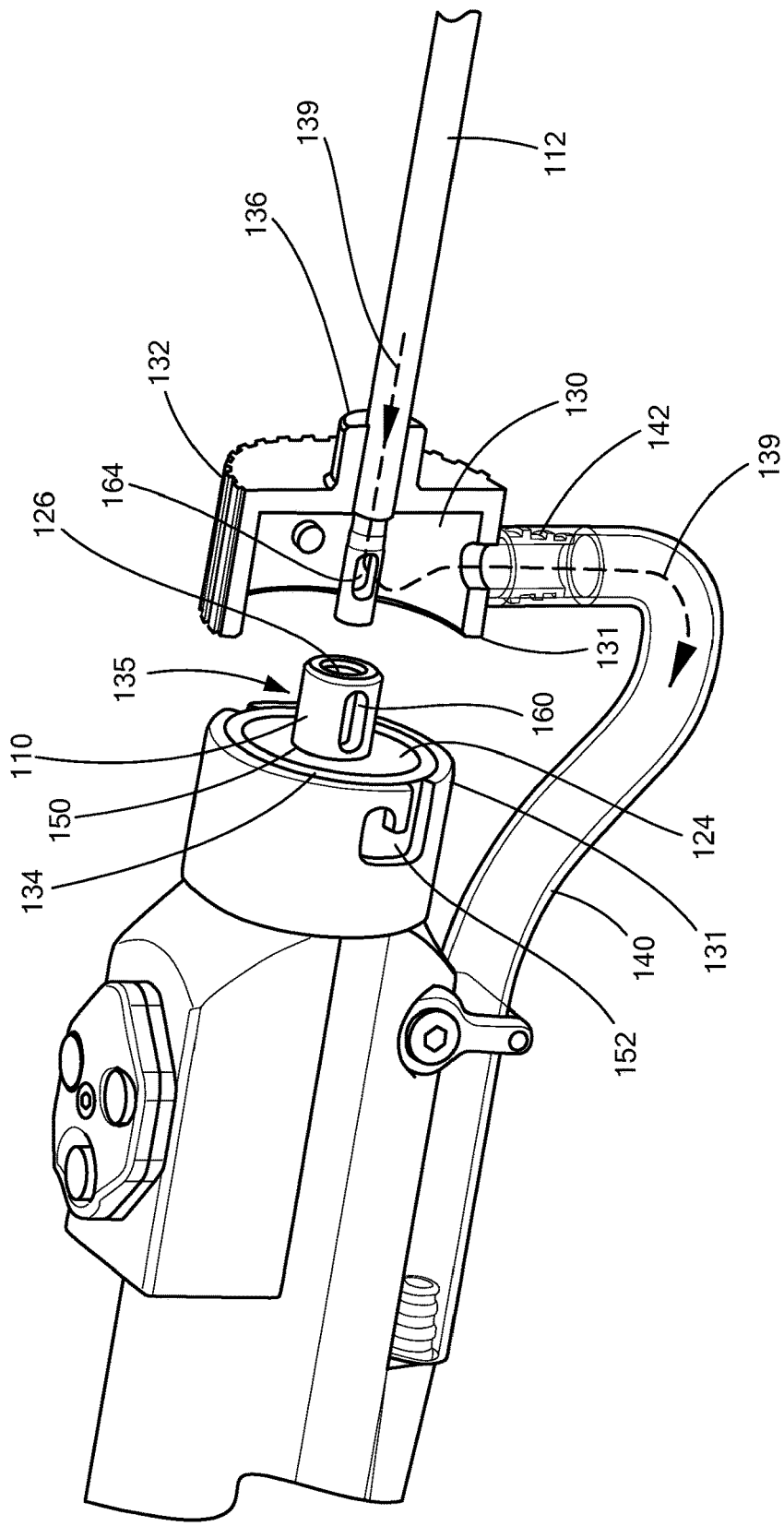
FIG. 3a is a closer view of the MDU and attachable resection device of FIG. 2.
Figure 3B:
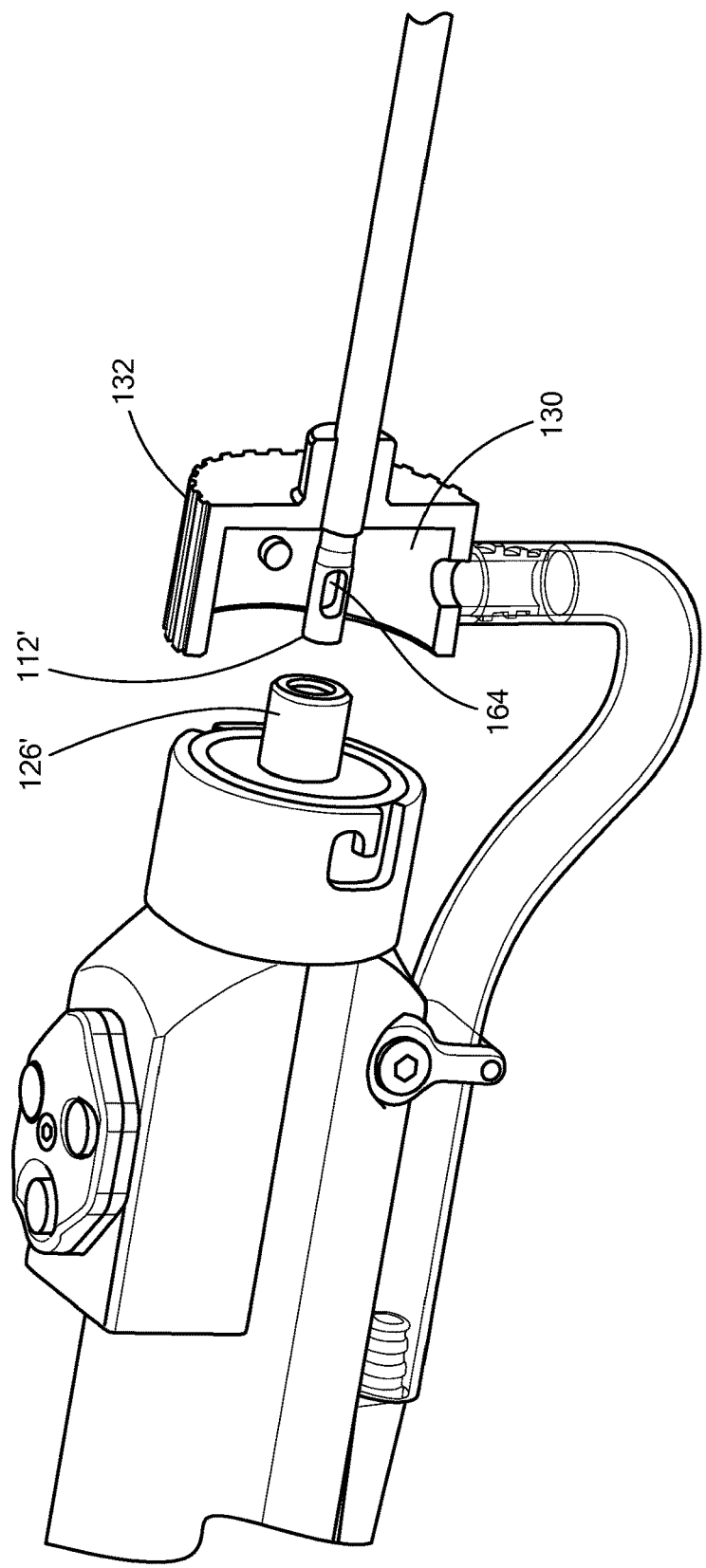
FIG. 3b shows an alternate engagement for the resection device of FIG. 3.

FIG. 2 is a perspective view of the external MDU as disclosed herein, and FIGS. 3a and 3b are a closer perspective view of the MDU of FIG. 2. Referring to FIGS. 2 and 3a, the surgical drive apparatus 100 as disclosed herein includes an external rotating shaft 110 adapted for engagement with a resectioning device 112. The resectioning device 112 may be any suitable surgical appliance, such as a blade or burr operable for surgical intervention when rotated. The apparatus 100 includes a drive unit 120 having a motor disposed in a motor chamber 122, such that the motor is rotationally coupled to the external rotating shaft 110 and the rotating shaft extends through an end 124 of the motor chamber 122. The rotating shaft 110 further includes a noncircular receptacle or protrusion 126 on the rotating shaft 110 for conveying rotary motion from the motor drive to the resectioning device 112. In the example arrangement, the noncircular receptacle is an oval shape, but any suitable rotary connection, such as square, hex (shown below in FIG. 5), pin arrangement, etc. may suffice. Rotary movement imparted by the rotating shaft 110 drives the resectioning device 112 for cutting or drilling movements at a surgical site.

A suction chamber 130 is defined by an interior of a detachable cap 132, in which the front end 124 of the motor chamber 122 is receptive to the cap 132 for sealing engagement with the drive unit 120. The cap 132 engages around the end 124 of the motor chamber 122 for providing a sealing engagement. A sealing ring 134 is disposed circularly around the rotating shaft 110 on the end 124 of motor chamber 122, in which the cap 132 is receptive to the sectioning device 112 and adapted for a sealing engagement with the end 124 of the drive unit 120 for providing a seal for a fluid path 139. The resectioning device 112 extends through the cap 132 for rotational movement relative to the cap 132 and fluid communication with the suction chamber 130, such that the rotating shaft 110 engages the resectioning device 112 for rotation therewith. The resection device 112 extends through a cap seal 136 opposite the sealing ring 134 for sealing the rotational coupling between the cap 132 and the sectioning device 112.

An outflow tube 140 is in fluid communication with the suction chamber 130 for completing the fluid path 139 to the resectioning device 112 via the suction chamber 130. A shaft passage 162 pulls material from a cannulated interior of the shaft, and mates or aligns with a corresponding fluidic passage 160 on the rotating shaft. Suction is generally created by applying a low pressure source to the outflow tube 140, which provides the fluid path 139 to the suction chamber 130 via a fitting 142 for evacuating surgical material extracted via the sectioning device 112. The surgical device is typically cannulated for continuing the fluid path to an interface region 113 where a cutting edge or other surgically operative component of the blade or burr is disposed.

The motor chamber 122 further includes a motor seal 150 disposed around the rotating shaft 112 between the motor chamber 122 and the suction chamber 130, such that the motor seal 150 prevents fluid communication between the motor chamber 122 and the suction chamber 130 but still permits rotation of the rotating shaft 110. The suction chamber 130 therefore separates the fluid path 139 from the motor chamber 122. The cap 132 defining the suction chamber 130 may further include a pin and groove 152 locking mechanism, including at least one pin or groove disposed on the motor chamber 122 and adapted to engage a complementary pin or groove disposed on the detachable cap 132. In this manner, a complete fluid path 139 from the outflow tube 140 through the suction chamber 130 and to the surgical site at the interface region 113 is provided via a cannulation in the sectioning device 112, without directing the fluid path 139 to the motor chamber 122 and associated voids and crevices that may be problematic for reuse sterilization. A suction port 142 couples to the suction chamber 130 and is adapted for connection of a low pressure source for evacuating the suction chamber 130, such as a surgical pump to remove abraded tissue, bone and fluids.

A sealable coupling 131 closes between the drive unit housing 120 and the suction chamber 130 and allows the suction to be directed to the cannulated interior of the rotary resectioning device 112, and a rotational seal between the drive unit housing 120 and the suction chamber 130 separates the low pressure source from the drive unit and housing by restricting the evacuated fluidic path to the suction chamber 130. The rotational seal and sealable coupling 130 define a fluidic path for evacuation of surgical material, which is separated from the drive unit and housing so as to not contaminate the non-disposable drive unit. Subsequent attachment of a suction device coupled to the suction port 14 generates the low pressure and applies suction for receiving evacuated surgical material from the suction chamber 130.

The fluidic path 139 is therefore defined by the rotational (motor) seal 150 and sealable coupling 130 for directing the low pressure source for evacuation of surgical material through the rotary device, such that the fluidic path is separated from the drive unit and housing. The fluidic path passes through the suction chamber 130 and out through the fitting 142 to the outflow tube 140, rather than the drive unit housing. The internals of the drive unit housing 120 are devoid of fluidic suction pathways and associated bends and corers that require cleaning between uses.

The engaging receptacle further comprises a fluidic passage 160 configured for directing the low pressure from the suction chamber 130 to the rotary device 112, typically through a cannulation in the shaft. In the example shown, the fluidic passage 164 further comprises an orifice on the receptacle, such that the orifice is adapted to align with a complementary orifice on the rotary device 12 for evacuating surgical material driven by suction from the low pressure.

FIG. 3b shows an alternate engagement for the resection device of FIG. 3a. Referring to FIGS. 3a and 3b, the protrusion 126 has a shorter depth such that an engaging end 112' of the resection tool 112 engages without obscuring the shaft passage 162. The shaft passage 162 therefore requires no corresponding passage 160 on the protrusion 126 for accommodating the fluid path.

Figure 4:
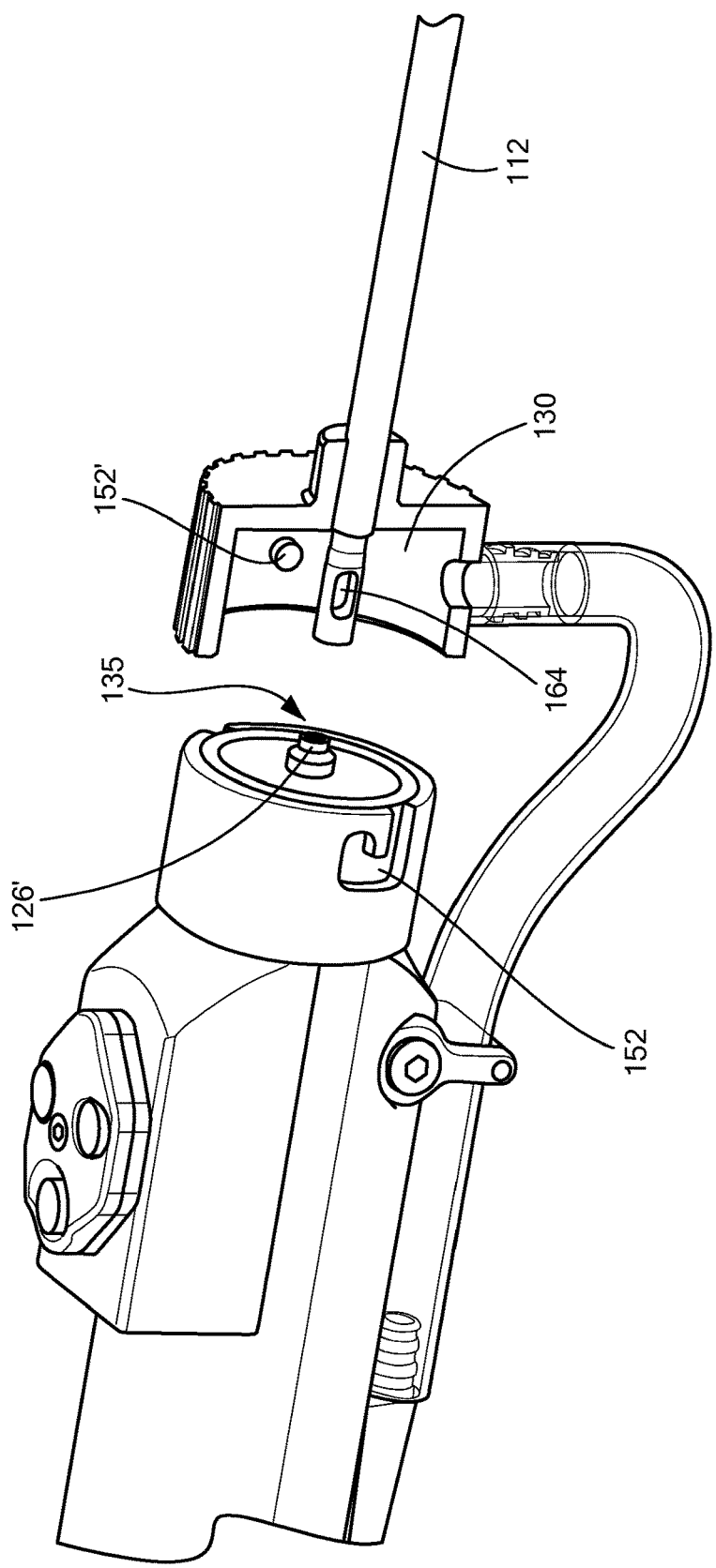
FIG. 4 is a view of the external MDU with a protruding drive feature.

FIG. 4 is a view of the external MDU with a protruding drive feature. Referring to FIGS. 2 and. 4, the protrusion 126 may be a solid protrusion 110' adapted to engage the interior, rather than the exterior of the resectioning device 112. The shaft passage 162 then allows suctioned material to be expelled into the suction chamber 130 before the protrusion 126' would obstruct the cannulation 164. In the example configuration, the sealable coupling further comprises a detachable cap attaching or engaging to the front surface of the drive motor housing. The detachable cap 132 is configured for selective engagement with the front surface, such that the sealable coupling 131 is defined by a compression between the detachable cap and the front surface 135. In one configuration, the sealable coupling 131 is formed by a pin 152' and groove 152 locking mechanism, including at least one pin disposed on the detachable cap 132 and adapted to engage the groove 152, the groove disposed on the motor chamber. Alternatively, the groove 152 may be on an interior of the detachable cap 132 and the pin disposed on the motor chamber (housing) 120.

Figure 5:
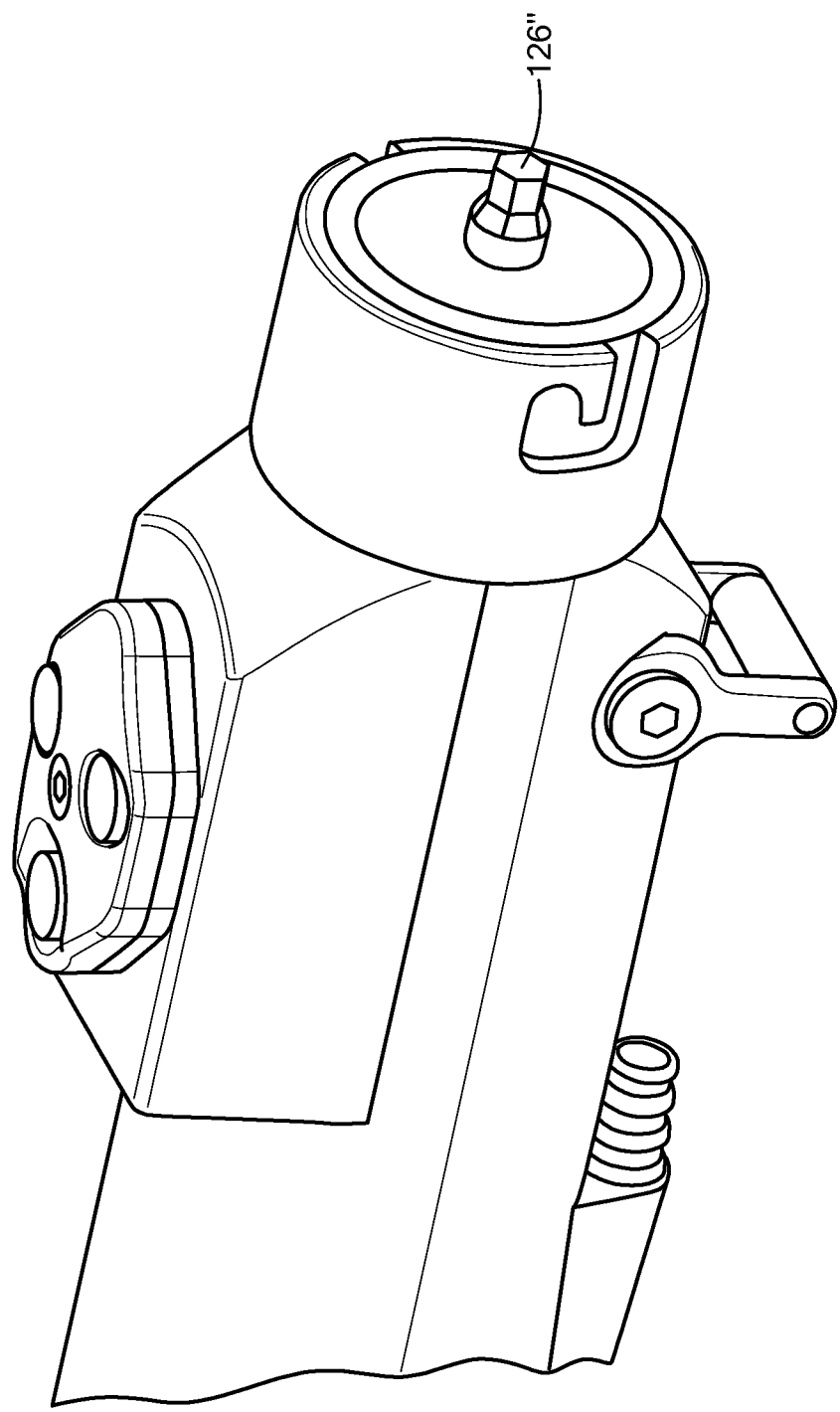
FIG. 5 is a view of the external MDU with a hex drive feature.

FIG. 5 is a view of the external MDU with a hex drive feature. An alternate configuration employs a hex shaped protrusion 110'', rather than an oval shape 110', for transmitting rotation via the engagement between the rotating shaft 110 and corresponding engagement 126. The sealable coupling 131 includes a resilient, circumferential region, or sealing ring 134, around the front surface 135 on the drive unit for engaging the cap 132 in a compressive, sealing manner.

Figure 6:
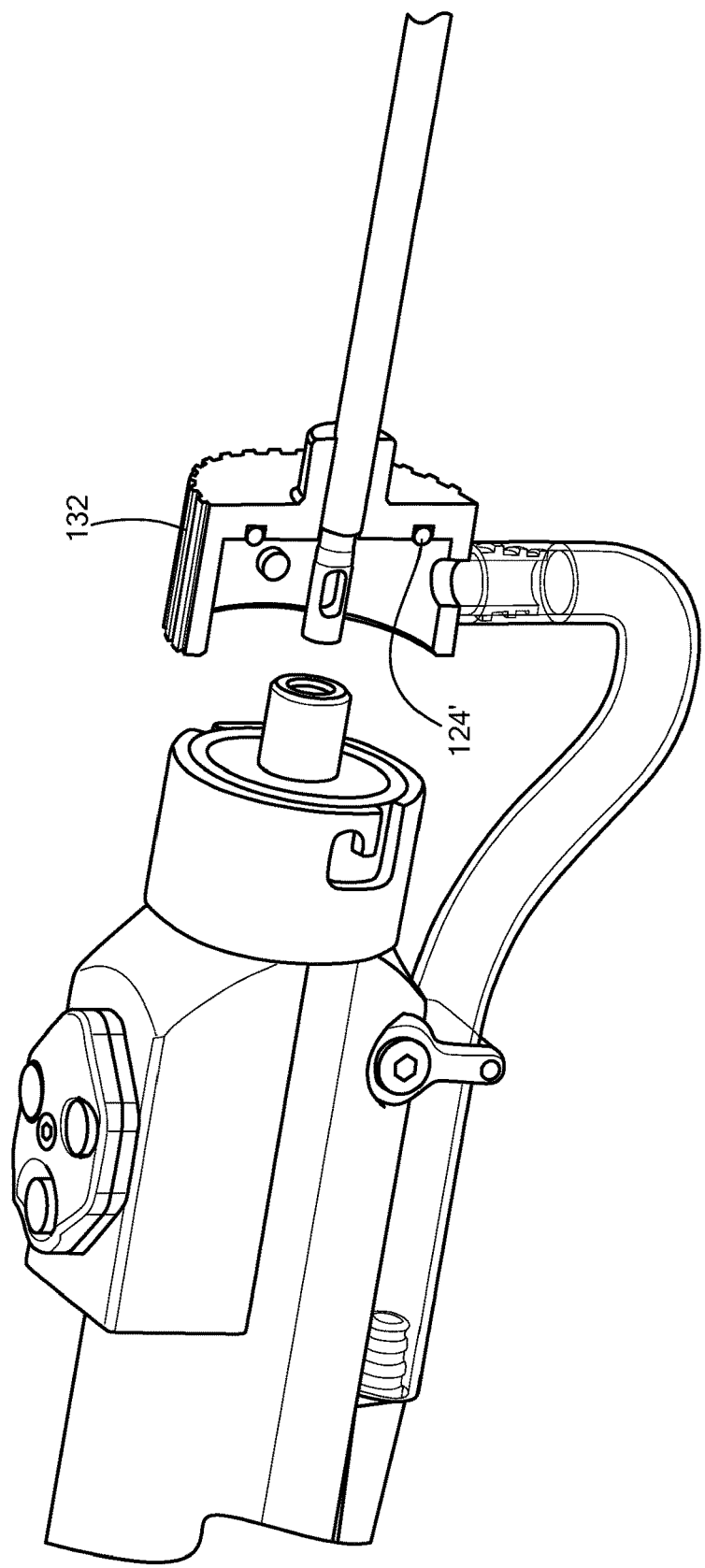
FIG. 6 shows an alternate seal location for the MDU of FIG. 5.

FIG. 6 shows an alternate seal location for the MDU of FIG. 5. A cap ring 124' seals the suction chamber rather than the sealing ring 134. Therefore, the sealable coupling further comprises a resilient sealing ring 134 adapted for compression between the front surface 135 and the engaged cap 132.

In an alternate configuration, the external drive may utilize a collet type chuck to secure the disposable blades, or the external drive may incorporate a snap feature to secure the blade or burr. In further contrast to conventional approaches, advantages of the disclosed approach include the following. The external drive MDU is easier to clean because it avoids an internal cavity with hard to reach areas that may hold contaminants Conventional reprocessing of blades becomes challenging due to the integrated fitting and outflow tubing. The disclosed one piece adapter simplifies the blade/burr assembly, and no latch is required.

While the system and methods defined herein have been particularly shown and described with references to embodiments thereof, it will be understood by those skilled in the art that various changes in form and details may be made therein without departing from the scope of the invention encompassed by the appended claims.

What is claimed is:
1. A surgical drive apparatus, comprising:
an external rotating shaft coupled to a resectioning device;
a drive unit having a motor disposed in a motor chamber, the motor rotationally coupled to the external rotating shaft, the external rotating shaft extending through a distal end of the motor chamber, and the distal end of the motor chamber defines an exterior surface of the drive unit;
a cap defining an interior volume, the cap telescoping, over the exterior surface of the drive unit;
a suction chamber defined by the interior volume of the cap and the exterior surface of the drive unit;
the resectioning device coupled to the external rotating shaft and extending through the cap;
the resectioning device configured to rotate relative to the cap and be in fluid communication with the suction chamber, the external rotating shaft configured to provide rotational movement to the resectioning device; and
an outflow tube in fluid communication with the suction chamber by way of the cap, the outflow tube defining a fluid path to the resectioning device via the suction chamber.

2. The apparatus of claim 1 further comprising a noncircular protrusion on the external rotating shaft configured to convey rotary motion from the motor to the resectioning device.

3. The apparatus of claim 1 further comprising a sealing ring disposed circularly around the external rotating shaft on the exterior surface of the drive unit, the cap receptive to the resectioning device and configured to create a sealed interior defined by the exterior surface of the drive unit and the interior volume of the cap.

4. The apparatus of claim 1 further comprising a motor seal disposed around the external rotating shaft between the motor chamber and the suction chamber, the motor seal preventing fluid communication between the motor chamber and the suction chamber.

5. The apparatus of claim 1 wherein the suction chamber separates the fluid path from the motor chamber.

6. The apparatus of claim 1 wherein the resectioning device is a blade or burr operable for surgical intervention when rotated.

7. The apparatus of claim 1 further comprising a pin and groove locking mechanism, including at least one pin disposed on the motor chamber and configured to engage a groove, the groove disposed on the cap.

* * * * *